US012611388B1

(12) United States Patent
Allen

(10) Patent No.: US 12,611,388 B1
(45) Date of Patent: Apr. 28, 2026

(54) WEIGHT LOSS FORMULATION AND METHODS

(71) Applicant: Gregory Seth Allen, Gilbert, AZ (US)

(72) Inventor: Gregory Seth Allen, Gilbert, AZ (US)

( * ) Notice: Subject to any disclaimer, the term of this patent is extended or adjusted under 35 U.S.C. 154(b) by 979 days.

(21) Appl. No.: 17/827,497

(22) Filed: May 27, 2022

Related U.S. Application Data

(63) Continuation of application No. PCT/US2022/031411, filed on May 27, 2022.

(60) Provisional application No. 63/194,045, filed on May 27, 2021.

(51) Int. Cl.

| | |
|---|---|
| ***A61K 31/137*** | (2006.01) |
| ***A61K 31/12*** | (2006.01) |
| ***A61K 31/485*** | (2006.01) |
| ***A61K 31/519*** | (2006.01) |
| ***A61P 3/04*** | (2006.01) |

(52) U.S. Cl.
CPC ............ *A61K 31/137* (2013.01); *A61K 31/12* (2013.01); *A61K 31/485* (2013.01); *A61K 31/519* (2013.01); *A61P 3/04* (2018.01)

(58) Field of Classification Search
CPC ......... A61P 3/04; A61K 31/137; A61K 31/12; A61K 31/485; A61K 31/519
See application file for complete search history.

(56) References Cited

U.S. PATENT DOCUMENTS

| | | | | |
|---|---|---|---|---|
| 8,071,557 B2 * | 12/2011 | Najarian | .............. | A61K 31/415 514/23 |
| 9,016,221 B2 * | 4/2015 | Brennan | ................... | A61L 2/02 428/141 |
| 2019/0022051 A1 | 1/2019 | Vath | | |
| 2020/0338078 A1 | 10/2020 | Zemel | | |

FOREIGN PATENT DOCUMENTS

| | | | | |
|---|---|---|---|---|
| WO | 2004091546 | | 10/2004 | |
| WO | 2009080691 | | 7/2009 | |
| WO | WO 2019/165208 | * | 8/2019 | ............... A61K 9/70 |
| WO | 2020036970 | | 2/2020 | |

* cited by examiner

*Primary Examiner* — Erich A Leeser
(74) *Attorney, Agent, or Firm* — Pacer K. Udall; Booth Udall, PLC

(57) ABSTRACT

The disclosure relates to compositions comprising a phentermine and a unicyclic aminoketone and methods of use thereof. The methods of use include inducing weight loss or reducing weight gain in a human subject. The unicyclic aminoketone may be diethylpropion or bupropion. In some embodiments, the compositions further include tadalafil or naltrexone.

13 Claims, 5 Drawing Sheets

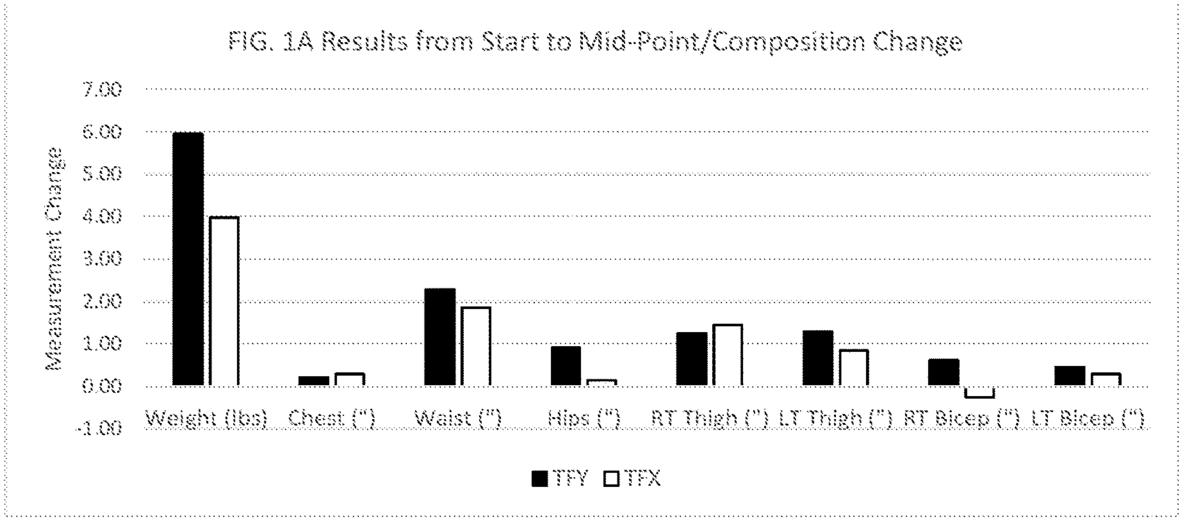
FIG. 1A Results from Start to Mid-Point/Composition Change
Measurement Change
7.00
6.00
5.00
4.00
3.00
2.00
1.00
0.00
-1.00
Weight (lbs)
Chest (")
Waist (")
Hips (")
RT Thigh (")
LT Thigh (")
RT Bicep (")
LT Bicep (")
TFY
TFX
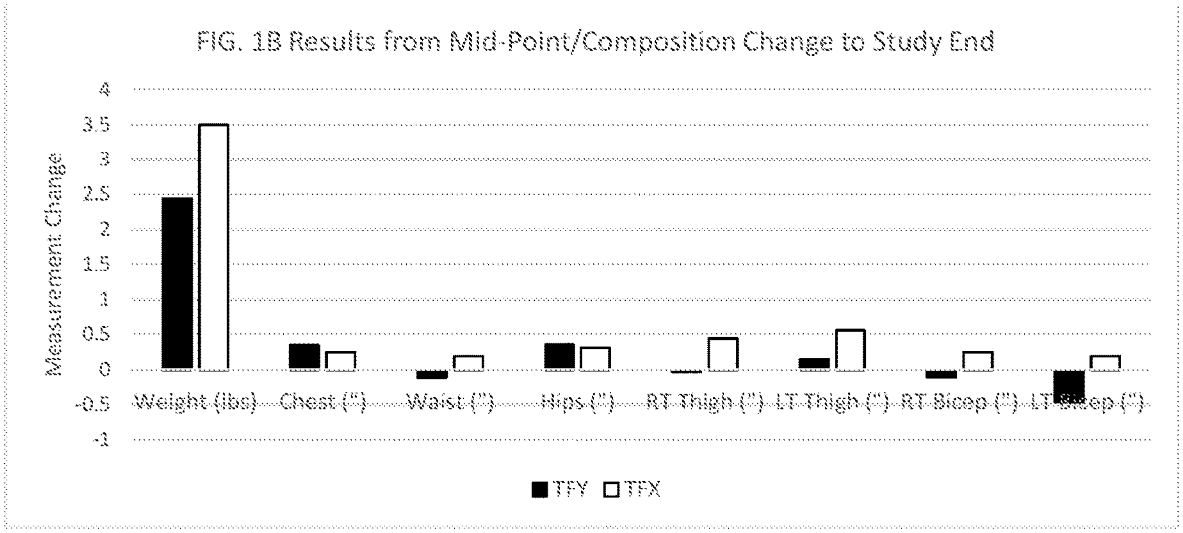
FIG. 1B Results from Mid-Point/Composition Change to Study End
Measurement Change
4
3.5
3
2.5
2
1.5
1
0.5
0
-0.5
-1
Weight (lbs)
Chest (")
Waist (")
Hips (")
RT Thigh (")
LT Thigh (")
RT Bicep (")
LT Bicep (")
TFY
TFX

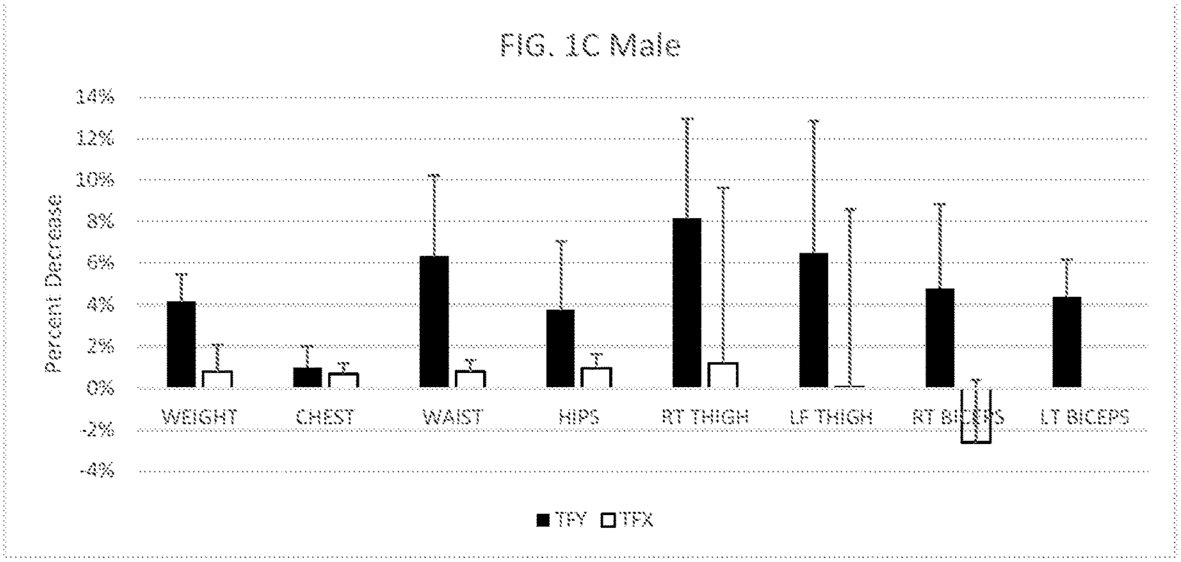
FIG. 1C Male
14%
12%
10%
8%
6%
4%
2%
0%
-2%
-4%
Percent Decrease
WEIGHT
CHEST
WAIST
HIPS
RT THIGH
LF THIGH
RT BICEPS
LT BICEPS
TFY
TFX
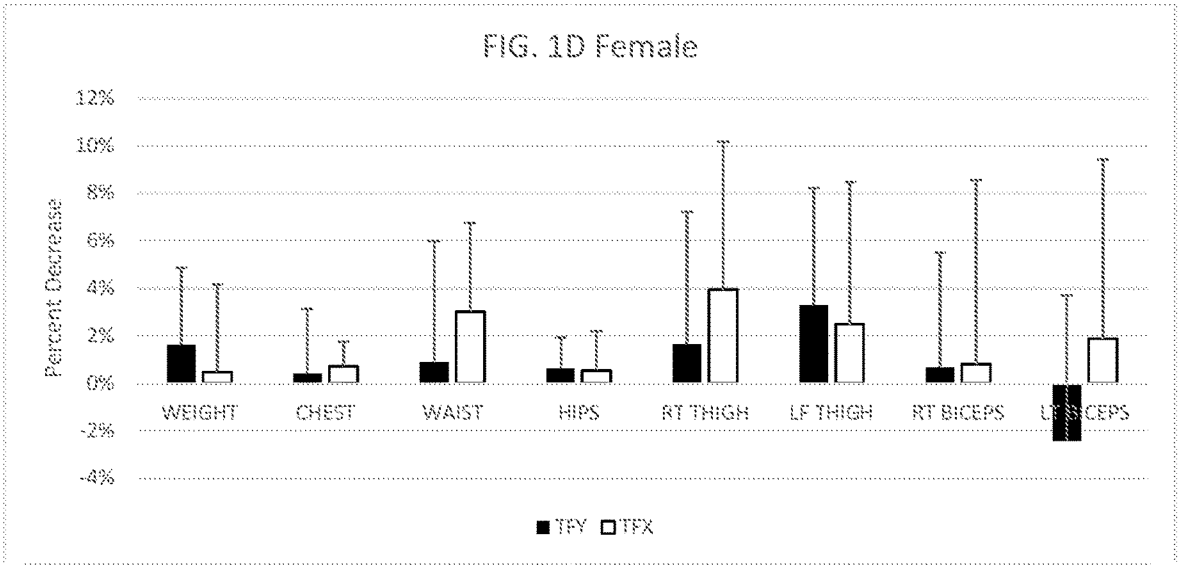
FIG. 1D Female
12%
10%
8%
6%
4%
2%
0%
-2%
-4%
Percent Decrease
WEIGHT
CHEST
WAIST
HIPS
RT THIGH
LF THIGH
RT BICEPS
LT BICEPS
TFY
TFX

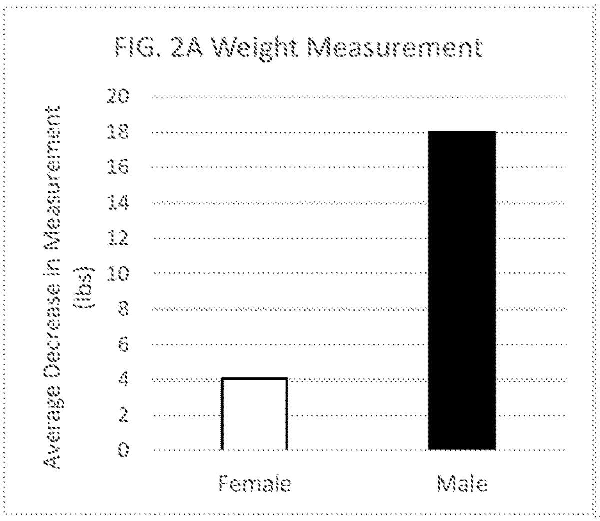
FIG. 2A Weight Measurement
Average Decrease in Measurement (lbs)
20
18
16
14
12
10
8
6
4
2
0
Female
Male

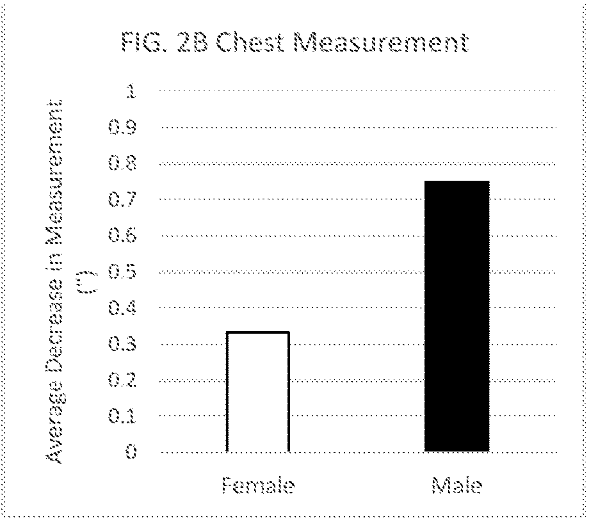
FIG. 2B Chest Measurement
Average Decrease in Measurement (")
1
0.9
0.8
0.7
0.6
0.5
0.4
0.3
0.2
0.1
0
Female
Male

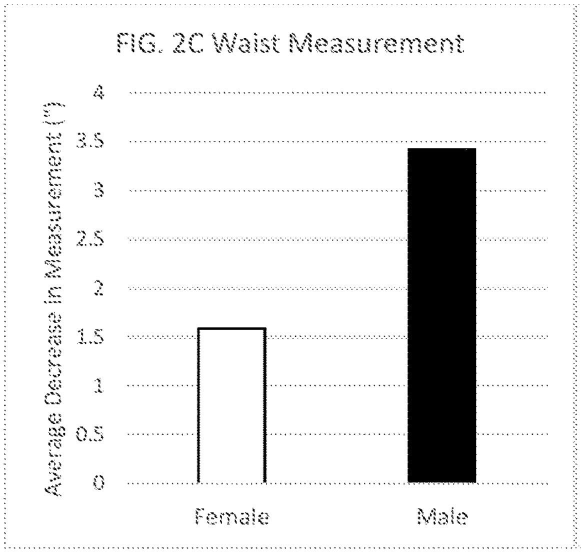
FIG. 2C Waist Measurement
Average Decrease in Measurement (")
4
3.5
3
2.5
2
1.5
1
0.5
0
Female
Male

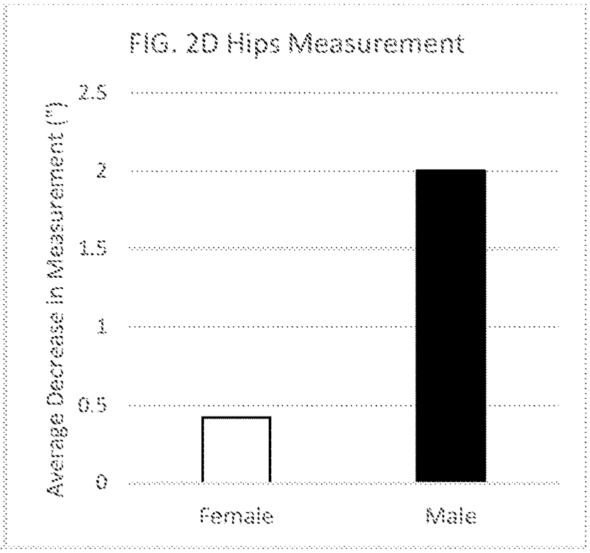
FIG. 2D Hips Measurement
Average Decrease in Measurement (")
2.5
2
1.5
1
0.5
0
Female
Male

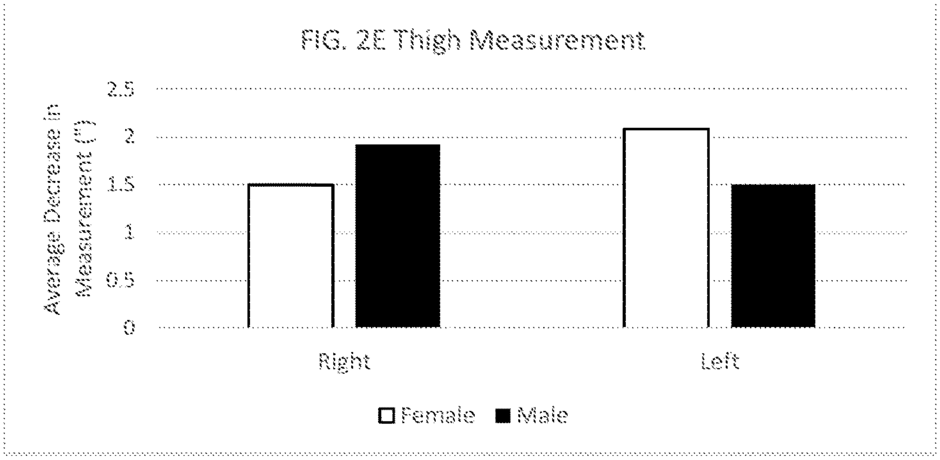
FIG. 2E Thigh Measurement
Average Decrease in Measurement (")
2.5
2
1.5
1
0.5
0
Right
Left
Female
Male

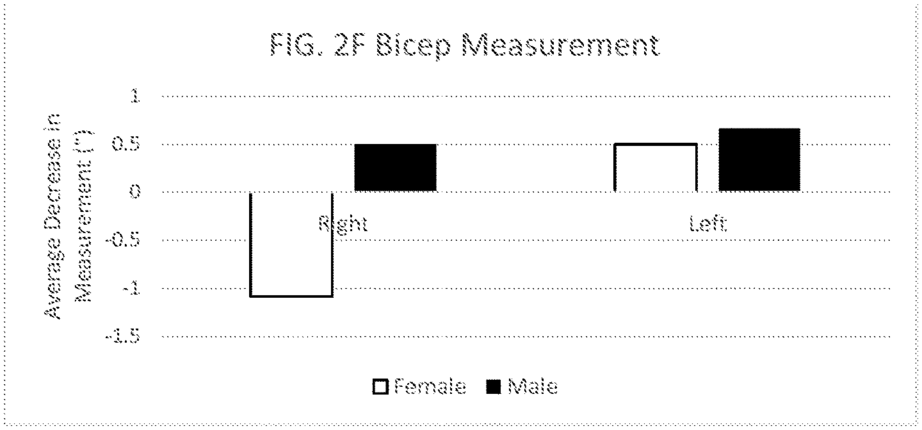
FIG. 2F Bicep Measurement
Average Decrease in Measurement (")
1
0.5
0
-0.5
-1
-1.5
Right
Left
Female
Male
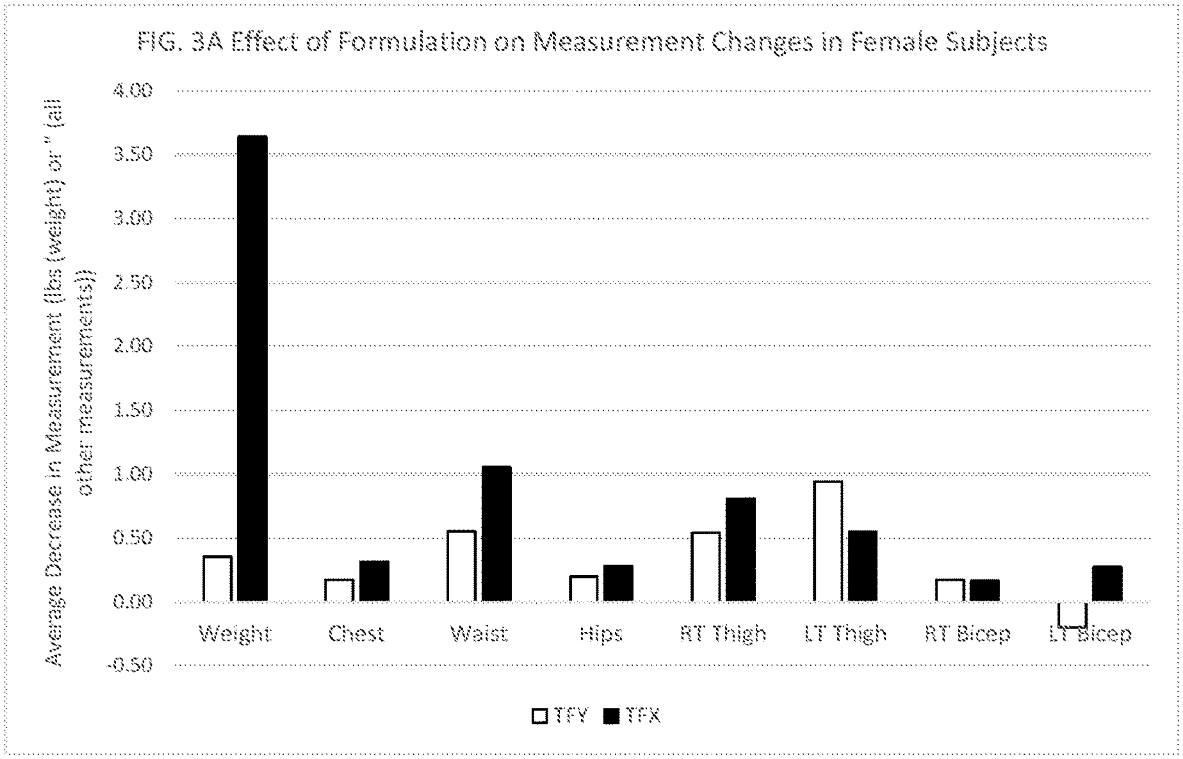
FIG. 3A Effect of Formulation on Measurement Changes in Female Subjects
Average Decrease in Measurement (lbs (weight) or " (all other measurements))
4.00
3.50
3.00
2.50
2.00
1.50
1.00
0.50
0.00
-0.50
Weight
Chest
Waist
Hips
RT Thigh
LT Thigh
RT Bicep
LT Bicep
TFY
TFX

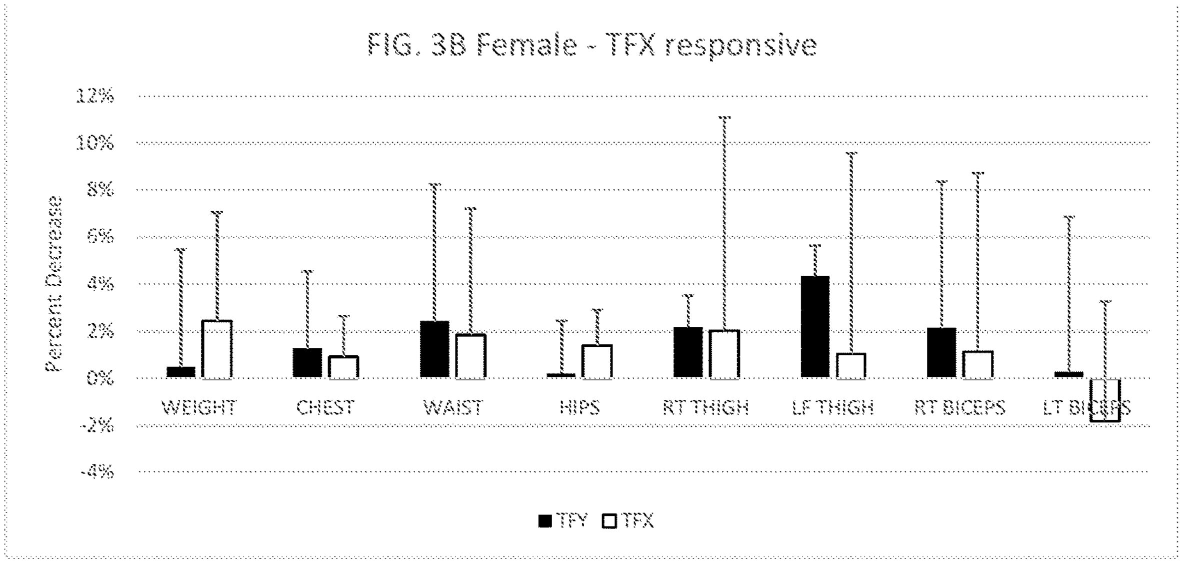
FIG. 3B Female - TFX responsive
Percent Decrease
12%
10%
8%
6%
4%
2%
0%
-2%
-4%
WEIGHT
CHEST
WAIST
HIPS
RT THIGH
LF THIGH
RT BICEPS
LT BICEPS
TFY
TFX
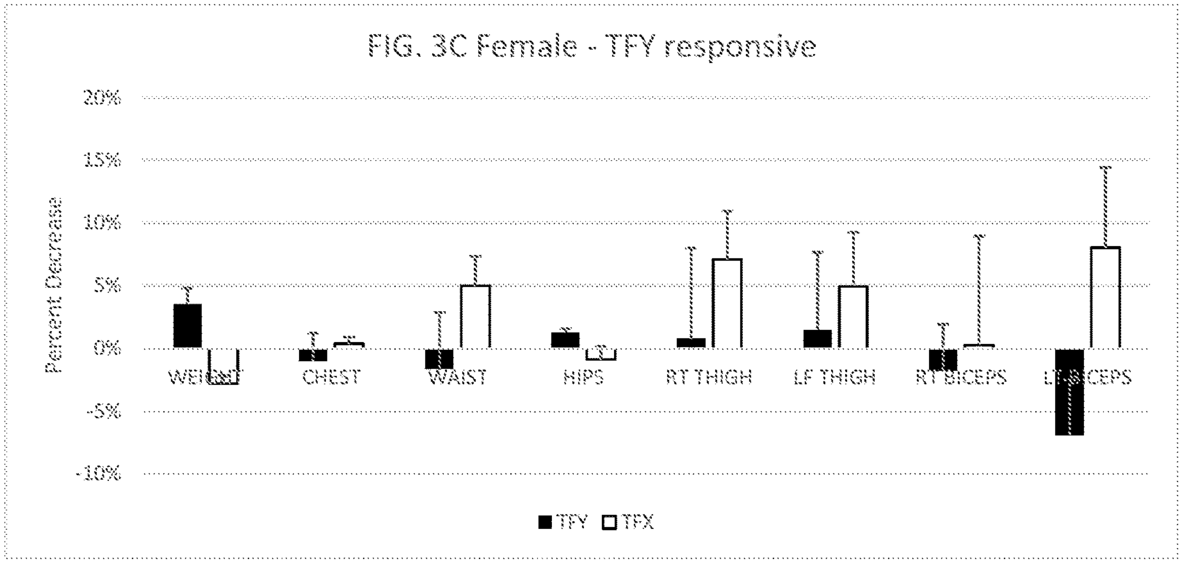
FIG. 3C Female - TFY responsive
Percent Decrease
20%
15%
10%
5%
0%
-5%
-10%
WEIGHT
CHEST
WAIST
HIPS
RT THIGH
LF THIGH
RT BICEPS
LT BICEPS
TFY
TFX

WEIGHT LOSS FORMULATION AND METHODS

CROSS REFERENCE TO RELATED APPLICATIONS

The present application is a continuation of PCT/US22/31411, filed May 27, 2022, which claims priority to U.S. Provisional Patent Application No. 63/194,045, filed May 27, 2021, the contents of which are hereby incorporated by reference in their entireties.

FIELD OF THE INVENTION

The present invention relates to formulations for inducing weight loss.

BACKGROUND OF THE INVENTION

Weight management is an important aspect of a healthy life. In the US, the market for products and services to aid weight loss is over $72 billion and is expected to continue through for the next few years. The market for products and services has grown to meal replacements, prescription, dietary or nutritional supplement, surgeries, and supposedly healthier ingredients. However, in spite of all of these options, obesity and being overweight remains a mostly unmanageable problem. It does not help that around 90% of medical pathologies in humans relate affect people's weight. However, a common thread for problematic weight gain or the inability to manage a health body weight has been overeating. Unfortunately, the current interventions to treat overeating is either often ineffective or has significant side effects. Thus, alternatives are needed for better managing the overeating aspect of weight management.

SUMMARY OF THE INVENTION

Described are compositions for and method of inducing weight loss or preventing weight gain in human subjects. The composition comprises phentermine and a unicyclic aminoketone having the structure of formula (I), wherein X is —H or a halo, Y is —H or $C_1$-$C_3$ alkyl, and Z is a $C_1$-$C_4$ alkyl.

Formula (I)

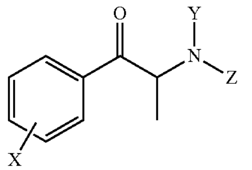

In some aspects, the composition comprise comprises 10-40 mg of the phentermine. In some embodiments, the composition comprises 25-75 mg of the unicyclic aminoketone.

In some embodiments, the composition is specific for inducing weight loss or preventing weight gain in male subjects. The unicyclic aminoketone in such compositions is diethylpropion. In some aspects, the composition further comprises tadalafil. In other embodiments, the composition is specific for inducing weight loss or preventing weight gain in female subjects. The unicyclic aminoketone in the composition is bupropion. In some aspects, the composition further comprises naltrexone. Also disclosed are the use of such compositions for inducing weight loss or preventing weight gain in a human subject.

In certain embodiments, the composition comprises 25-75 mg diethylpropion and 12.5-37.5 mg phentermine. In some aspects, the composition further comprises tadalafil, for example, 2.5-10 mg tadalafil. In particular embodiments, the composition comprises 25 mg diethylpropion; 12.5 mg phentermine; and 2.5 mg tadalafil; 50 mg diethylpropion; 25 mg phentermine; and 5 mg tadalafil; or 75 mg diethylpropion; 37.5 mg phentermine; and 10 mg tadalafil.

In other embodiments, the composition comprises 37.5-75 mg bupropion and 15-37.5 mg phentermine. In some aspects, the composition further comprises naltrexone, for example, 2-4 mg naltrexone. In particular embodiments, the composition comprises 37.5 mg bupropion; 15 mg phentermine; and 2 mg naltrexone; 50 mg bupropion; 20 mg phentermine; and 3 mg naltrexone; or 75 mg bupropion; 37.5 mg phentermine; and 4 mg naltrexone.

In some implementations, the methods of inducing weight loss or preventing weight gain in a human subject comprising administering to the human subject a composition comprising phentermine and a unicyclic aminoketone having the structure of formula (I), wherein X is —H or a halo, Y is —H or $C_1$-$C_3$ alkyl, and Z is a $C_1$-$C_4$ alkyl. In some aspects, the human subject is need of reaching a healthy body weight. Where the human subject is male, the unicyclic aminoketone administered is diethylpropion. In some aspects, the male human subject is further administered tadalafil. In certain implementations, tadalafil is administered in the same composition as phentermine and the unicyclic aminoketone. Where the human subject is female, the unicyclic aminoketone administered is bupropion. In some aspects, the female human subject is further administered naltrexone. In certain implementations, naltrexone is administered in the same composition as phentermine and the unicyclic aminoketone.

In some implementations, the method comprises administering 10-40 mg phentermine to the subject. In some aspects, the amount of phentermine administered 1.3-2.7 nmol/kg mg/kg body weight of the human subject or 0.15-0.25 mg/kg body weight of the human subject. In some implementations, the method comprises administering 25-75 mg of the unicyclic aminoketone. In some aspects, the amount of the unicyclic aminoketone administered is 0.35-0.45 mg/kg body weight of the human subject.

In particular implementations, the unicyclic aminoketone administered is diethylpropion. In such embodiments, the amount of diethylpropion administered is 25-75 mg. In some aspects, the amount of phentermine administered is 12.5-37.5 mg or 1.3-2.3 nmol/kg body weight of the human subject. In some implementations, the method further comprises administering to the human subject an amount of tadalafil, for example, 2.5-10 mg tadalafil, 0.02-0.1 mg tadalafil/kg body weight of the human subject, or 0.12-0.20 nmol tadalafil/kg body weight of the human subject.

In particular implementations, the unicyclic aminoketone administered is bupropion. In such embodiments, the amount of bupropion administered is 37.5-75 mg. In some aspects, the amount of phentermine administered is 15-37.5 mg or 1.5-2.7 nmol/kg body weight of the human subject. In some implementations, the method further comprises administering to the human subject an amount of naltrexone, for example, 2-4 mg naltrexone, 0.02-0.06 mg naltrexone/kg body weight of the human subject, or 0.14 mg to 0.24 nmol/kg body weight of the human subject.

BRIEF DESCRIPTION OF THE DRAWINGS

FIGS. 1A-1D compare changes in weight and the circumference of the chest, waist, hips, thighs, and biceps. FIG. 1A shows results from all subjects from the start of the study to the mid-point (when the subjects received a different weight loss composition). FIG. 1B shows the results from all subjects from the mid-point (when the subjects received the different weight loss composition) to the end of the study. FIG. 1C compares the changes in weight and the circumference of the chest, waist, hips, thighs, and biceps in the male subjects when they were given the TFY formulation or the TFX formulation. FIG. 1D compares the changes in the weight in weight and the circumference of the chest, waist, hips, thighs, and biceps in the female subjects they were given the TFY formulation or the TFX formulation.

FIGS. 2A-2F compare the effect of the TFY formulation (50 mg diethylpropion, 25 mg phentermine, and 5 mg tadalafil) between male and female subjects in the context of changes in weight (FIG. 2A) and the circumference of the chest (FIG. 2B), waist (FIG. 2C), hips (FIG. 2D), thighs (FIG. 2E), and biceps (FIG. 2F).

FIGS. 3A-3C compares the effect of the TFY formulation (50 mg diethylpropion, 25 mg phentermine, and 5 mg tadalafil) and TFX formulation (50 mg bupropion, 3 mg naltrexone, and 20 mg phentermine) on female subjects in the context of changes in weight and the circumference of the chest, waist, hips, thighs, and biceps. FIG. 3A shows a comparison of all female subjects.

FIG. 3B shows the comparison for female subjects who lost more weight on the TFX formulation.

FIG. 3C show the comparison for female subjects who only lost weight on the TFY formulation.

DETAILED DESCRIPTION OF THE INVENTION

Detailed aspects and applications of the invention are described below in the drawings and detailed description of the invention. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the invention. It will be understood, however, by those skilled in the relevant arts, that the present invention may be practiced without these specific details. It should be noted that there are many different and alternative configurations, devices and technologies to which the disclosed inventions may be applied. The full scope of the inventions is not limited to the examples that are described below.

The singular forms "a," "an," and "the" include plural referents unless the context clearly dictates otherwise. Thus, for example, reference to "a step" includes reference to one or more of such steps.

As used herein, the term "overeating" refers to the consumption of excess food in relation to the energy that an organism expends or expels, which can lead to weight gaining and obesity over the long term. In some aspects, overeating refers to eating past the point of being full, which may result in heart burn, increased heart rate, stomach distension, and excess gas.

As used herein, the term "healthy body weight" refers to a body weight that results in a body mass index of between 18 to 25, for example between 18.5 and 24.9. In some aspects, a human subject with a healthy body weight also has a waist circumference of less than 40 inches, for example, less than 40 inches for males and less than 35 inches for non-pregnant females. In other aspects, the term "healthy body weight" also refers to a human subject with less than 32% (by weight) body fat, for example, less than 25% body fat for males and less than 32% for females. In still other aspects, the term "healthy body weight" refers to a human subject with a desirable percentage of muscle mass by weight. For example, for males between the ages of 18-35 years with a healthy body weight, their percentage of muscle mass is 40-44%. For males between the ages of 36-55 years with a healthy body weight, their percentage of muscle mass is 36-40%. For males between the ages of 56-75 years with a healthy body weight, their percentage of muscle mass is 32-35%. For males over the age of 76 years with a health body weight, their percentage of muscle mass is less than 31%. For females between the ages of 18-35 years with a healthy body weight, their percentage of muscle mass is 31-33%. For females between the ages of 36-55 years with a healthy body weight, their percentage of muscle mass is 29-31%. For females between the ages of 56-75 years with a healthy body weight, their percentage of muscle mass is 27-30%. For females over the age of 76 years with a health body weight, their percentage of muscle mass is less than 26%.

The disclosure relates to helping people overcome their problems with overeating address one of the biggest obstacles for maintaining a healthy body weight, for inducing weight loss, or reducing or preventing weight gain. Accordingly, disclosed herein are formulation for and methods of controlling the quantity of food consumed by a human subject to induce weight loss or reduce or prevent weight gain. The human subjects in need of inducing weight loss and/or in need of reducing or preventing weight gain are subjects in need of treatment for obesity or weight-related medical problems, for example overeating. In some aspects, the subjects are overweight but not yet obese. Also disclosed are methods of inducing weight loss, reducing weight gain, or preventing weight gain in human subjects in need of thereof, for example, subjects who are overweight, obese, or in need of treatment for other weight-related medical problems.

The disclosed composition comprises phentermine and a unicyclic aminoketone having the structure of formula (I), wherein X is —H or a halo, Y is —H or $C_1$-$C_3$ alkyl, and Z is a $C_1$-$C_4$ alkyl:

Formula (I)

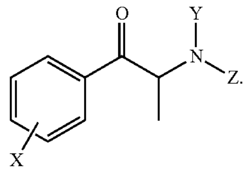

In some aspects, Z is a tertiary butyl group. In some aspects, Y is a $C_2$ alkyl and/or Z is a $C_2$ alkyl. In certain embodiments, the composition comprises phentermine and bupropion. In other embodiments, the composition comprises phentermine and diethylpropion.

The disclosed methods comprise administering to a human subject in need of inducing weight loss and/or in need of reducing or preventing weight gain a phentermine and administering to the human subject a unicyclic aminoketone having the structure of formula (I), wherein X is —H or a halo, Y is —H or $C_1$-$C_3$ alkyl, and Z is a $C_1$-$C_4$ alkyl. In certain implementations, the human subject is administered a composition comprising phentermine and the unicyclic aminoketone. In some embodiments, the unicyclic aminoketone is diethylpropion or bupropion. In some aspects, the unicyclic aminoketone administered to the human subject at a dose of 0.2-1.0 mg/kg body weight, while the phentermine is administered to the human subject at a dose of 0.1-0.5 mg/kg body weight. In certain embodiments, the dose of the unicyclic aminoketone and of phentermine administered are respectively 0.35-0.45 mg/kg body weight and 0.15-0.25 mg/kg body weight. In other embodiments, the dose of the unicyclic aminoketone and of phentermine administered are respectively 0.6-0.8 mg/kg body weight and 0.3-0.4 mg/kg body weight.

For female subjects, three facets effect their weight and health: emotional eating, hormonal eating, and exercised-induced overeating. Emotional eating refers the situation when everyday stressors with family or work increase causes women turn to food for comfort, which in turn causes them to overeat. Hormonal eating refers to the situation during women's menses when they typically have a craving to eat foods that make them feel better, which are often high in carbohydrates and sugars. Exercise-induced overeating refers to the situation when subjects turn to exercise to lose weight, but the accompanying increased metabolism from increased exercise increases the sensation of hunger and leads the subjects to eat more food. Overeating due to increased exercise; many women turn to exercise when they want to lose weight. With increased exercise, the metabolism increases. As the metabolism increases so does hunger, making it more difficult to control, leading to overeating.

For male subjects, the biggest problem with maintaining a healthy body weight is controlling the quantity of food consumption and stress eating. While there are weight-loss medications on the market that can help male subjects control the quantity of food consumed and minimize stress eating, these medications have significant and inconvenient side effects. One such problem is erectile dysfunction, which contributed to depression in the male subject. In turn, men are not compliant to their weight management plans, as they would rather stay fat than lose their ability to perform sexually.

Thus, in some embodiments, the disclosed composition further comprises a third therapeutic agent to address sex-specific concerns related to weight-loss management. Accordingly, the disclosed methods further comprise administering to the human subject a third therapeutic agent. For male-specific concerns, the third therapeutic agent is tadalafil. In some aspects, the dose of tadalafil administered to the human subject is 0.02 mg to 0.1 mg/kg body weight, for example, 0.05 to 0.07 mg/kg body weight. In certain implementations, the unicyclic aminoketone used in combination with tadalafil is diethylpropion. Thus, in some embodiments, the dose of diethylpropion administered to the human subject is 0.2-0.6 mg/kg body weight, for example, 0.35-0.45 mg/kg body weight. For female-specific concerns, the third therapeutic agent is naltrexone. In some aspects, the dose of naltrexone administered to the human subject is 0.02-0.06 mg/kg body weight, for example, 0.03 to 0.05 mg/kg body weight. In certain implementation the unicyclic aminoketone in combination with naltrexone is bupropion. Thus, in some embodiments, the dose of bupropion administered to the human subject is 0.5-1.0 mg/kg body weight, for example, 0.6 to 0.8 mg/kg body weight.

While a composition or combination therapy comprising tadalafil is best suited for a male subject, the composition or combination therapy could also be administered to a female subject to result in weight loss and reduced measurements for the chest, waist, hips, thigh, and bicep circumferences. However, there is a subset of female subjects who do not lose weight with the composition comprising tadalafil but instead would lose weight with the composition comprising naltrexone (FIGS. 3A-3C). Also for some female subject, the composition comprising tadalafil are better tolerated, as they experienced fewer or less severe side effects while using the composition comprising tadalafil rather than the composition comprising naltrexone. Accordingly, in some methods of inducing weight loss, reducing weight gain, or preventing weight gain in human subjects in need of thereof (for example, a female subject), the method may first comprise administering to the subject a first composition comprising phentermine, naltrexone, and the unicyclic aminoketone to determine if the patient loses weight, and then administering to the subject a second composition comprising phentermine, tadalafil, and the unicyclic aminoketone if the patient does not lose weight when administered the first composition.

The doses of phentermine, the unicyclic aminoketone, tadalafil, and naltrexone administered to the human subject can change during the course of the weight loss plan. The range of the unicyclic aminoketone administered to the human subject is 25-75 mg. The range of phentermine administered to the human subject is 12-38 mg. The range of tadalafil administered to the human subject is 2.5-10 mg. The range of naltrexone administered to the human subject is 2-4 mg. For example, in some aspects, the composition administered to the human subject comprises 37.5 mg bupropion, 2 mg naltrexone, and 15 mg phentermine. This may be a starting dose. In other aspects, the composition comprises 50 mg bupropion, 3 mg naltrexone, and 20 mg phentermine. This may be the maintenance dose. In still other aspects, the composition comprises 75 mg bupropion, 4 mg naltrexone, and 37.5 mg phentermine. This composition would provide the high dose of these medications for managing body weight. As another example, in some aspects, the composition administered to the subject comprises 25 mg diethylpropion, 12.5 mg phentermine, and 2.5 mg tadalafil. This may be a starting dose. In other aspects, the composition comprises 50 mg diethylpropion, 25 mg phentermine, and 5 mg tadalafil. This may be the maintenance dose. In still other aspects, the composition comprises 75 mg diethylpropion, 37.5 mg phentermine, and 10 mg tadalafil. This composition would provide the high dose of these medications for managing body weight.

As shown in the Examples, combining three different FDA-approved medications produced unexpected benefits maintaining a healthy body weight, for inducing weight loss, or reducing or preventing weight gain for female human subject. The unexpected benefits include lower doses of each medication to get the desire effect (for example, controlling emotional overeating, hormonal overeating, and exercise-induced overeating) and reduced side effects of each medication. The described compositions are effective in inducing weight loss and/or in reducing or preventing weight gain at doses much lower than the existing doses used for these medications. The FDA-approved doses of bupropion are between 75 mg to 522 mg, dose of diethylpropion is 75 mg daily, of phentermine are 8 mg three time a day or 15 to 37.5 mg daily, of naltrexone is 50 mg daily, and of tadalafil are 2.5 mg to 5 mg daily or 2.5 mg to 20 mg when needed but not more than once a day.

The present invention is further illustrated by the following example that should not be construed as limiting. The contents of all references, patents, and published patent applications cited throughout this application, as well as the Figures, are incorporated herein by reference in their entirety for all purposes.

EXAMPLES

The disclosure is further illustrated by the following examples that should not be construed as limiting. The contents of all references, patents, and published patent applications cited throughout this application, as well as the Figures, are incorporated herein by reference in their entirety for all purposes.

1. Experimental Design

Eleven subjects (8 females, 3 males) were given the TFX formulation or the TFY formulation over the course of four weeks. The subjects were given one formulation for two weeks and then switched to the other formulation for two weeks. The subjects were instructed to take one dose of the formulation in the morning, about 30 minutes after breakfast. All of the male subjects and three of female subjects were given the TFY formulation first followed by the TFX formulation. The other five subjects were given the TFX formulation first followed by the TFY formulation. Of these give female subjects, two received the starter TFY formulation instead of the maintenance dose formulation.

One dose of the TFX formulation comprises 50 mg bupropion, 3 mg naltrexone, and 20 mg phentermine. This is the maintenance dose formulation. The reported side effects of the TFX formulation are mild to severe headache, jitteriness, restless legs, difficulty sleeping, fatigue, lightheadedness, constipation, and heartburn.

One dose of the TFY formulation comprises 50 mg diethylpropion, 25 mg phentermine, and 5 mg tadalafil. The reported side effects of the TFY formulation are headache, jitteriness, restless legs, difficulty sleeping, fatigue, lightheadedness, constipation, nausea, heartburn, and acne. Two of the subjects could not tolerate the TFY formulation for the full two weeks. They were moved to the starter dose, which comprises 25 mg diethylpropion, 12.5 mg phentermine, and 2.5 mg tadalafil.

2. Comparison of Measure Changes Between the Formulations

The efficacy of the TFY formulation is greater in male subjects than female subjects, as shown in FIGS. 1A and 1*i*, where the efficacy of the TFY formulation seemed reduced due to female subjects switching from the TFX formulation to the TFY formulation. When the changes in weight and circumference were reported as percent change and evaluated according to the sex of the subjects (as in FIGS. 1C and 1D), the TFY formulation effected a greater percentage of weight loss and reduced body mass in male subjects than female subjects. On the other hand, the TFX formulation produced more consistent reductions in weight and body mass in female subjects (compare FIGS. 1C and 1D).

3. TFY Formulation Effects: Male vs. Female

As shown in FIG. 2A, male subjects exhibited a much more robust response to the TFY formulation and experienced an average weight loss of 18 pounds, compared to an average weight loss of 4 pounds for all female subjects. Male subjects also exhibited a more significant decrease in all other measurements taken compared to female subjects when the subjects were administered the TFY formulation (see FIGS. 2B-2F). Men experienced an average decrease of 0.75 inches in their chest measurement compared to an average decrease of 0.5 inches for female subjects, an average decrease of 3.4 inches in the waist measurement compared to an average decrease of 1.6 inches for female subjects, and an average decrease of 2 inches in their hip measurement compared to an average decrease of 0.5 inches for female subjects. Similar trends were measured in the thighs and biceps, where men experienced more significant decreases in measurements in the thighs and biceps relative to female subjects.

4. Effects of TFY and TFX Formulations on Females

As shown in FIG. 3A, female subjects taking the TFX formulation experienced significantly greater weight loss, losing an average of 3.64 pounds in comparison to women who took the TFY formulation, who lost an average of 0.36 pounds. Female subjects taking the TFX formulation also experienced greater decreases in chest, waist, and hips measurements in comparison to women taking the TFY formulation.

When the change is shown as a percentage, it is apparent that the female subjects could be divided into to two subgroups—one that is responsive to the TFX formulation (FIG. 3B) and that is responsive to the TFY formulation (FIG. 3C). For female subjects responsive to the TFY formulation, the percentage of weight loss is comparable to that of male subjects on the TFY formulation. However, the trend for reduction of body mass as indicated by reduced circumference of the waist, hips, thighs, or biceps, seem to be more consistent with the TFX formulation for all female subjects (see FIGS. 1D, 3B, and 3C). Accordingly, female subjects unable to lose weight on the TFX formulation may benefit from treatment with the TFY formulation.

The invention claimed is:

1. A composition comprising:

phentermine; and a unicyclic aminoketone having the structure:

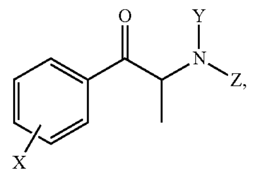

wherein:

X is —H or a halo,

Y is —H or $C_1$-$C_3$ alkyl, and

Z is a $C_1$-$C_4$ alkyl.

2. The composition of claim 1, wherein the composition comprises 10-40 mg of the phentermine.

3. The composition of claim 1, wherein the composition comprises 25-75 mg of the unicyclic aminoketone.

4. The composition of claim 1, wherein the unicyclic aminoketone is diethylpropion.

5. The composition of claim 4, wherein the composition comprises 25-75 mg diethylpropion.

6. The composition of claim 5, wherein the composition comprises 12.5-37.5 mg phentermine.

7. The composition of claim 4, further comprising tadalafil.

8. The composition of claim 7, wherein the composition comprises 2.5-10 mg tadalafil.

9. The composition of claim 1, wherein the unicyclic aminoketone is bupropion.

10. The composition of claim 9, wherein the composition comprises 37.5-75 mg bupropion.

11. The composition of claim 10, wherein the composition comprises 15-37.5 mg phentermine.

12. The composition of claim 9, further comprising naltrexone.

13. The composition of claim 12, wherein the composition comprises 2-4 mg naltrexone.

* * * * *